(12) United States Patent
Nakao

(10) Patent No.: US 7,029,435 B2
(45) Date of Patent: Apr. 18, 2006

(54) ENDOSCOPE HAVING MULTIPLE WORKING SEGMENTS

(75) Inventor: Naomi L. Nakao, New York, NY (US)

(73) Assignee: Granit Medical Innovation, LLC, New York, NY (US)

( * ) Notice: Subject to any disclaimer, the term of this patent is extended or adjusted under 35 U.S.C. 154(b) by 0 days.

(21) Appl. No.: 10/687,401

(22) Filed: Oct. 16, 2003

(65) Prior Publication Data
US 2005/0085691 A1    Apr. 21, 2005

(51) Int. Cl.
*A61B 1/00* (2006.01)
(52) U.S. Cl. .................. 600/153; 600/104; 600/160
(58) Field of Classification Search ............. 600/104, 600/121, 123, 125, 153, 156, 160, 113
See application file for complete search history.

(56) References Cited

U.S. PATENT DOCUMENTS 5,630,782 A * 5/1997 Adair .................... 600/133
6,066,090 A * 5/2000 Yoon ..................... 600/113
6,179,776 B1 * 1/2001 Adams et al. ........... 600/121
6,328,730 B1 * 12/2001 Harkrider, Jr. .......... 604/523
6,352,503 B1 * 3/2002 Matsui et al. ........... 600/104

* cited by examiner

*Primary Examiner*—Beverly M. Flanagan
(74) *Attorney, Agent, or Firm*—R. Neil Sudol; Henry D. Coleman; William J. Sapone

(57) ABSTRACT

A flexible fiberoptic endoscope has an insertion member with a distal end portion split longitudinally into a plurality of independently operable working segments each provided with at least one longitudinally extending working channel. Visualization optics are provided in the working segments or a separate central segment surrounded by the working segments. A sheath temporarily joins the working segments to one another during an introduction procedure. The sheath is removed upon insertion of the endoscope, so that the working segments may be/separated from one another and independently maneuvered via proximal control heads to facilitate the performance of an endoscopic surgical procedure.

23 Claims, 9 Drawing Sheets

ENDOSCOPE HAVING MULTIPLE WORKING SEGMENTS

BACKGROUND OF THE INVENTION

This invention relates to flexible fiberoptic endoscopy. More particularly, this invention relates to a fiberoptic endoscope and a related endoscopy technique.

Flexible fiberoptic endoscopy is a minimally invasive procedure that is diagnostic for the most part. Certain minimal surgical procedures are being performed, but these are quite limited in scope. These surgical procedures include biopsy, polypectomy, and endoscopic mucosal resection (a recently introduced procedure). There are certain instruments used to endoscopically treat gastroesophageal reflux disorder (GERD. These instruments are large and clumsy and are, for the most part, attached to the endoscope rather than manipulated through its working channels.

The main reason for the inability to perform surgical procedures through a flexible fiberoptic endoscope is that the endoscope itself represents "one hand." One cannot suture (push and pull a needle), tie a knot, handle a cut, or control a bleeding vessel with only one hand. Two hands are required. During rigid laparoscopy, five different "hands" are used. There are four ports for instruments, and one port for the camera operator. Three different individuals perform the operation. Two handle two ports each, and a third manipulates the camera. Complicated surgical procedures are routinely performed through these thin tubes. There is currently a need for a flexible fiberoptic instrument that will enable the performance of flexible endoscopic surgery with two or more "hands."

OBJECTS OF THE INVENTION

It is an object of the present invention to provide an improved fiberoptic endoscope.

A more particular object of the present invention is to provide a flexible fiberoptic endoscope that facilitates the performance of multiple-hand surgical procedures.

Yet another object of the present invention is to provide an associated endoscopic method that enables the performance of relatively complex endoscopic surgical procedures.

These and other objects of the present invention will be apparent from the drawings and descriptions herein. Although it is believed that every object of the invention is achieved in at least one embodiment of the invention, there is not necessarily a single embodiment that achieves all of the objects of the invention.

SUMMARY OF THE INVENTION

Generally, a flexible endoscope pursuant to the present invention is composed of two or more elongate flexible distal segments joined at a position proximal to the distal end of these segments. Each segment may have light and visualization components along with working channels to facilitate medical procedures. Alternatively, there may be an additional, separate segment that alone contains the light and visualization components. Thus, where an endoscope has two working segments and a visualization segment, each working segment may have a semi-annular cross-section, while the visualization segment is cylindrical and centrally located, surrounded by the two working segments together. The semi-annular segments each include one or more biopsy or working channels for the introduction of flexible operating instruments. The cylindrical center segment may be provided with a channel for irrigation.

In any case, at a point half way or more proximally up the instrument and preferably about one-third of the endoscope length from its proximal end, the separate segments are joined to end in at least one head member carrying a control mechanism that is able to maneuver the working segments independently of each other and also direct light, visualization, suction, irrigation, and medical tools passed through the working channels in each of the segments.

The instrument is inserted into a patient as substantially one elongate flexible endoscope. The distal ends of the segments may be separably joined together to facilitate insertion into the body. Joining the distal segments may be done by a mechanical means utilizing a proximal control mechanism of the endoscope. For instance, securing of the distal segments may be accomplished by using a temporary joining member such as a sheath that can be split or torn away once the endoscope is properly inserted into the body cavity.

The sheath surrounds the two or more independent working segments at the distal end of the instrument and contains the segments in a tube shape that is easily inserted into a body cavity. The endoscope insertion member with the joined distal working segments is similar in overall geometric form and usage to conventional endoscopes. Controlling the orientation of the distal tip of the endoscope insertion member with the joined working segments may be accomplished by maneuvering one of the working segments, with the other segment(s) following by virtue of the entrainment imposed by the joining element (e.g., sheath). When the desired position inside the hollow organ is achieved, the sheath is pulled proximally, thereby exposing the distal end segments and separating the "hands" of the endoscope. As the sheath is pulled towards the head of the endoscope, it is torn away from the endoscope insertion member. Withdrawal of the endoscope from the patient after the working segments have been freed or separated from one another is easily performed and does not require a re-sheathing as a simple pulling action is all that is required to remove the instrument.

Pursuant to another feature of the present invention, the endoscope may have two or more proximal control heads. A preferred embodiment has two head members. Each head member has respective actuator mechanisms for controlling the corresponding distal segment. Thus, an endoscopist together with an assistant or another endoscopist performs a procedure in concert. The two heads control the respective hands or distal end segments in performing a single operation.

In the case where the distal working segments are "blind," i.e., without the light or camera components and there is a third endoscope insertion segment with these features, this third segment can be manipulated by a third operator. This procedure resembles the procedure followed during rigid laparoscopy.

The two or more endoscope insertion segments could be joined in such a way that one or more segment could be pulled or pushed independently of the others in the case that there is a need for one longer and one shorter segment.

Where there is a separate segment containing the light and visualization components, this segment may be provided with a longer proximal end so that the respective operator can stand at a distance from the two other operators so as not to interfere or crowd them.

Procedures that require two or more operators include suturing, cutting, tying, retracting of tissue or organs, and other surgical techniques. Most of these procedures cannot be performed with a conventional endoscope having a single unitary insertion member. One cannot easily tie a knot with one hand; two hands are required. The same is true for the other above-mentioned procedures. The split endoscope of the present invention will thus open the door to therapeutic flexible fiberoptic endoscopy. This will in turn enable the physician to perform surgery within the lumen instead of entering the hollow organ through the abdominal or chest cavity such as is done during open surgery or laparoscopy.

DETAILED DESCRIPTION OF THE PREFERRED EMBODIMENTS

Figure 1:
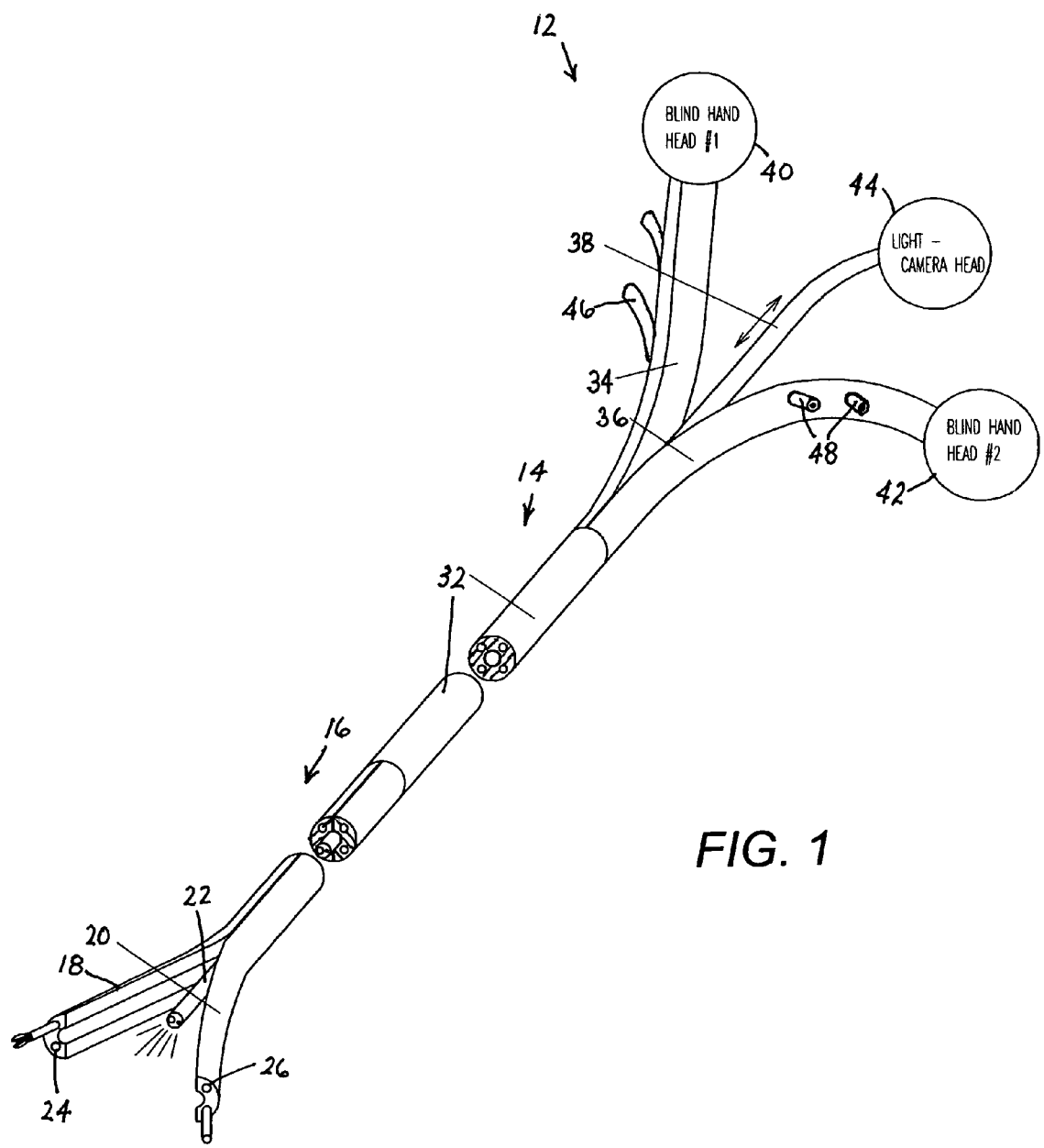
FIG. 1 is partially a schematic perspective view on a reduced scale and partially a block diagram of a flexible fiberoptic endoscope in accordance with the present invention.
Figure 2:
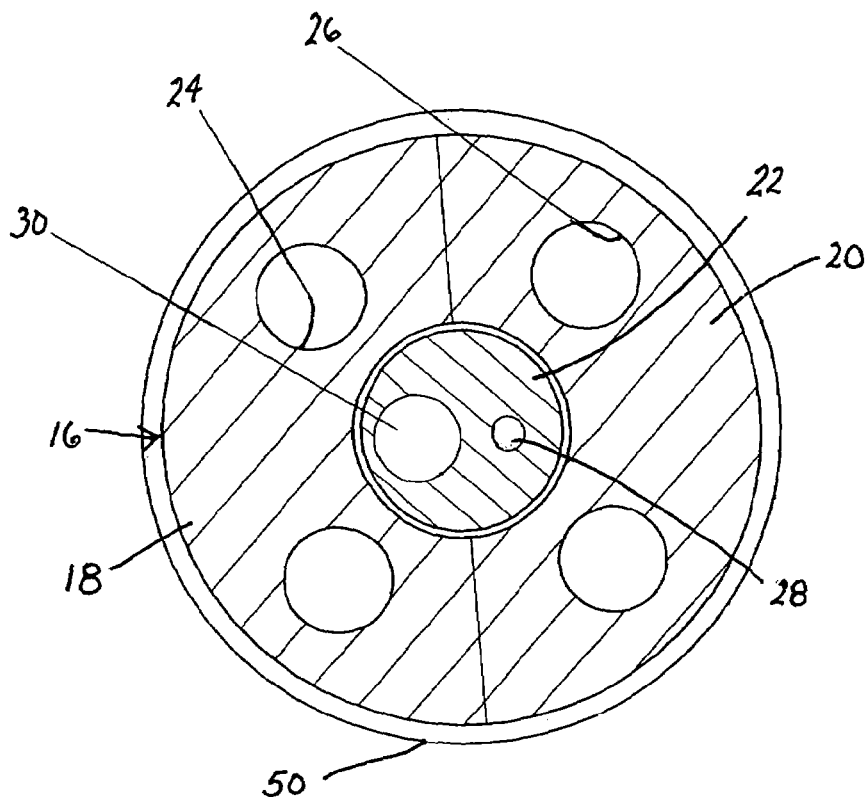
FIG. 2 is a schematic transverse cross-sectional view on an enlarged scale of the flexible fiberoptic endoscope of FIG. 1, showing distal-end working segments and a light and visualization component in a bound configuration surrounded by a sheath.
Figure 3:
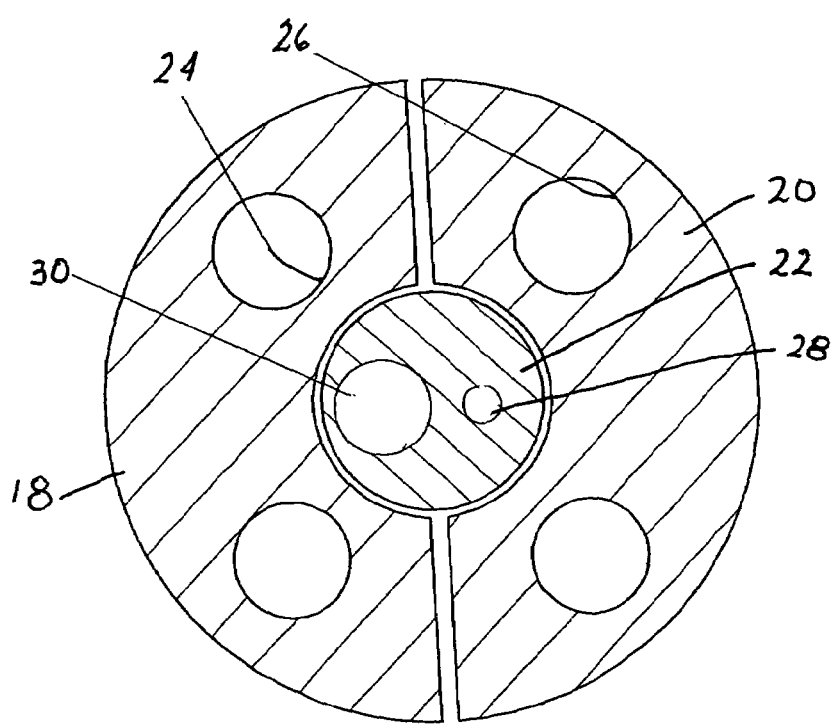
FIG. 3 is a view similar FIG. 2, showing the distal-end working segments and the light and visualization component of FIG. 2 without the sheath.

As depicted in FIG. 1, an endoscope 12 that is particularly useful for the performance of endoscopic surgical operations includes an insertion member 14 having a distal end portion 16 longitudinally split into a pair of working segments 18 and 20 and a central visualization segment 22. As shown in FIGS. 2 and 3, working segments 18 and 20 are each provided with a pair of longitudinal biopsy or working channels 24 and 26, whereas visualization segment 22 is provided with an illumination guide 28 and a lens 30 forming a portion of image transmission optics. The image transmission optics generally include a solid-state camera (not shown) generating an electrical image-encoding signal transmitted to a video monitor (not shown) for enabling visualization of a surgical site by operating surgeons or endoscopists. Visualization segment 22 may be additionally provided with a longitudinal channel (not illustrated) for conducting an irrigation liquid such as saline solution As further depicted in FIG. 1, working segments 18 and 20 are permanently bound to one another via a band 32 at a location at least as far in a proximal direction as a midpoint of the endoscope insertion member 14. Preferably, band 32 is located about one-third of the distance from the proximal end of the instrument.

At its proximal end, endoscope insertion member 14 divides into three separate sections 34, 36, and 38 that are connected to or continuous extensions of working segments 18 and 20 and visualization segment 22. Each section 34, 36, 38 is provided at a proximal end with a respective control head 40, 42, 44. Control heads 40, 42, 44 are provided with actuators such as rotatable knobs or joysticks (not shown) for maneuvering working segments 18 and 20 and optionally visualization segment 22. More particularly, control heads 40, 42, 44 are used to determine the orientation or curvature of working segments 18 and 20 and visualization segment 22. Proximal endoscope sections 34 and 36 are provided with ports 46 and 48 for the introduction of flexible endoscopic instruments into channels 24 and 26 of working segments 18 and 20.

One of more of working segments 18 and 20 and visualization segment 22 may be slidably secured to band 32. Where visualization segment 22 is slidable, proximal endoscope section 38 may be pulled in the proximal direction to provide more space for surgeons operating working heads 40 and 42 to conduct an endoscopic surgical operation via working segments 18 and 20.

As illustrated in FIG. 2, a sheath 50 surrounds distal end portion 16 of endoscope insertion member 14 at the onset of an endoscopic surgical procedure utilizing the endoscope 12 of FIG. 1. Sheath 50 serves to hold working segments 18 and 20, as well as visualization segment 22, in a compact tubular configuration for facilitating introduction into the patient. Upon a removal of sheath 50 from distal end portion 16 of endoscope insertion member 14, as shown in FIG. 3, working segments 18 and 20 are freed for independent maneuvering.

Sheath 50 may be a simple cylindrical film or web and is optionally provided along an inner surface with a coating of a lubricant such as silicone to facilitate a shifting of the sheath in a proximal direction to uncover and release working segments 18 and 20 and visualization segment 22 after the distal end portion 16 of endoscope insertion member 14 has been inserted into a hollow organ or body cavity of the patient. Alternatively, sheath 50 may be provided with one or more longitudinally extending tear strings (not illustrated) that are embedded in the synthetic resin material of the sheath at least in the area of distal end portion 16 and that extend to the proximal end of the endoscope, where the tear string may be manually grasped and pulled to uncoupled the sheath prior to a withdrawal thereof from the distal end portion 16 of the endoscope insertion member 14.

Figure 4A:
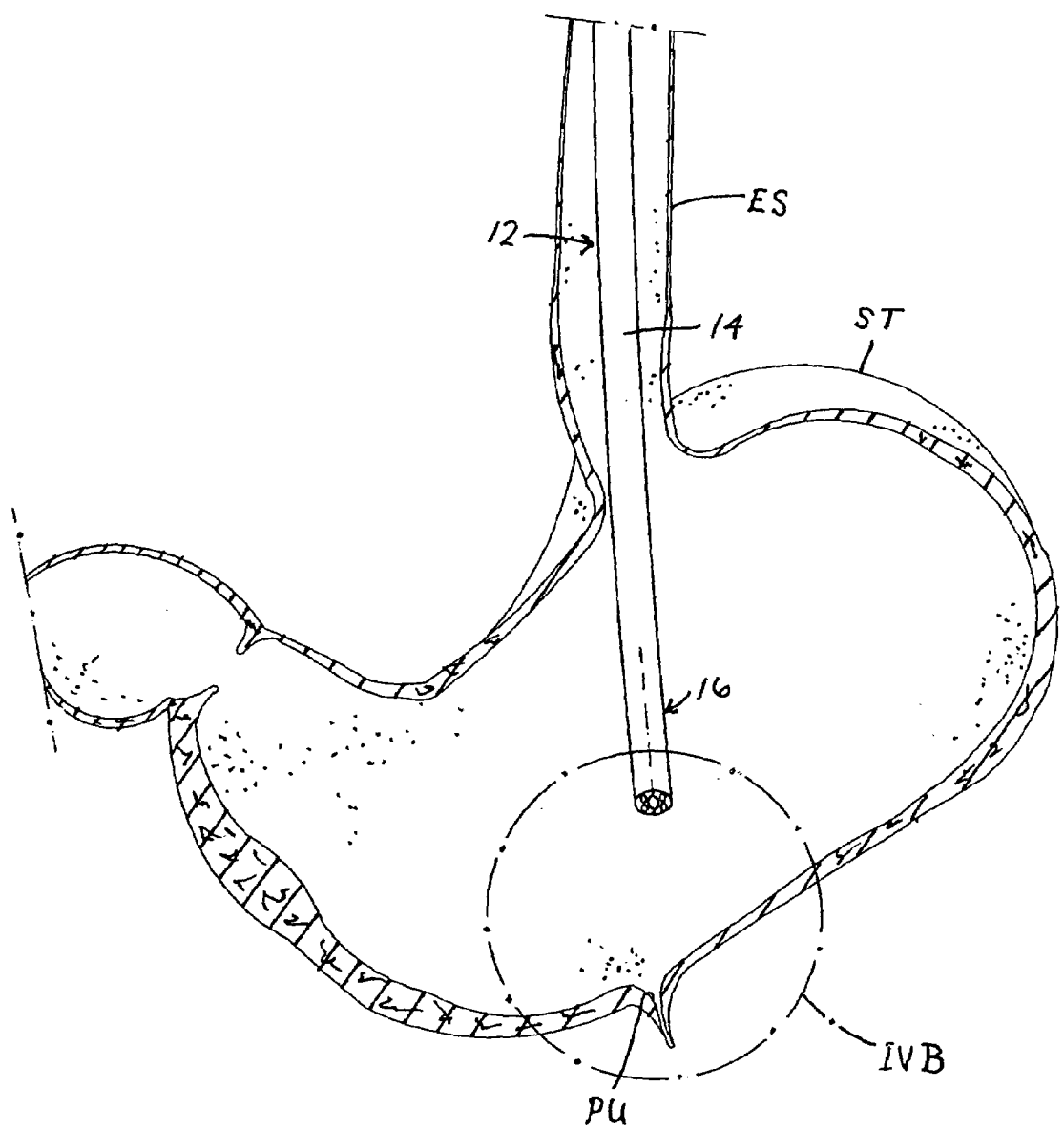
FIG. 4A is a cross-sectional view of a person's stomach, showing an initial stage in an endoscopic surgical operation in accordance with the present invention.

FIG. 4A shows a first step in an endoscopic surgical procedure utilizing endoscope 12. Insertion member 14 is introduced via a patient's esophagus ES into the patient's stomach ST. During the insertion procedure, working segments 18 and 20 are bound in a cylindrical configuration about visualization segment 22 by sheath 50 (not separately designated in FIG. 4A). Illumination and image transmission components 28 and 30 are used to inspect the stomach wall and to detect a perforated ulcer PU.

Figure 4B:
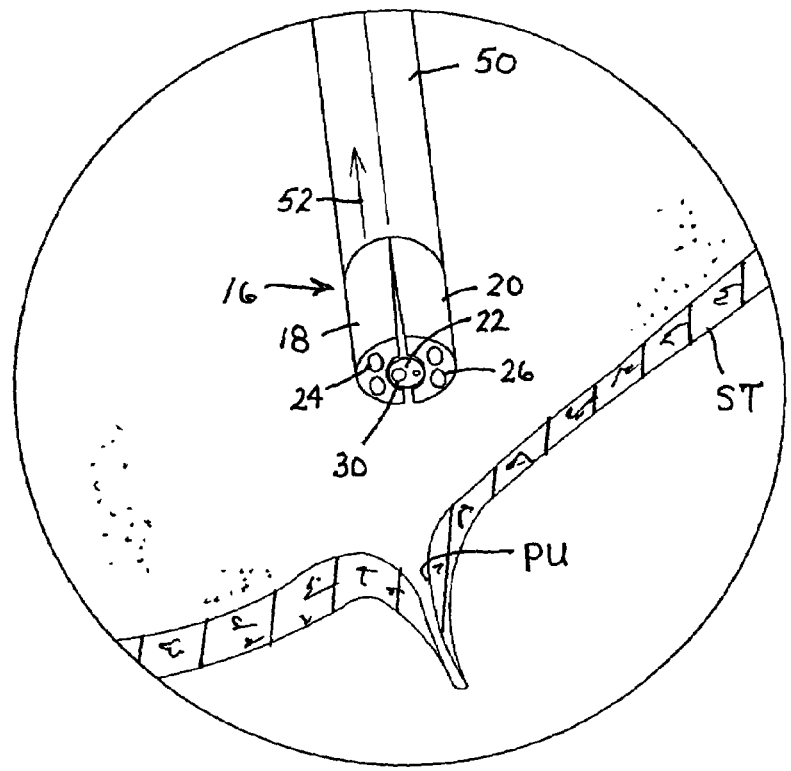
FIGS. 4B–4J are cross-sectional detail views of the area IVB in FIG. 4A, showing furthr successive steps in the endoscopic surgical procedure.

Upon the detection of ulcer PU, sheath 50 is pulled in the proximal direction, as indicated by arrow 52 in FIG. 4B, and withdrawn to release working segments 18 and 20 and thereby enable a separation thereof from one another and from visualization segment 22. Control heads 40 and 42 (FIG. 1) are manipulated by respective surgeons or endoscopists to maneuver working segments 18 and 20 into position facing ulcer PU on opposite sides thereof for performing an endoscopic suturing operation.

Figure 4C:
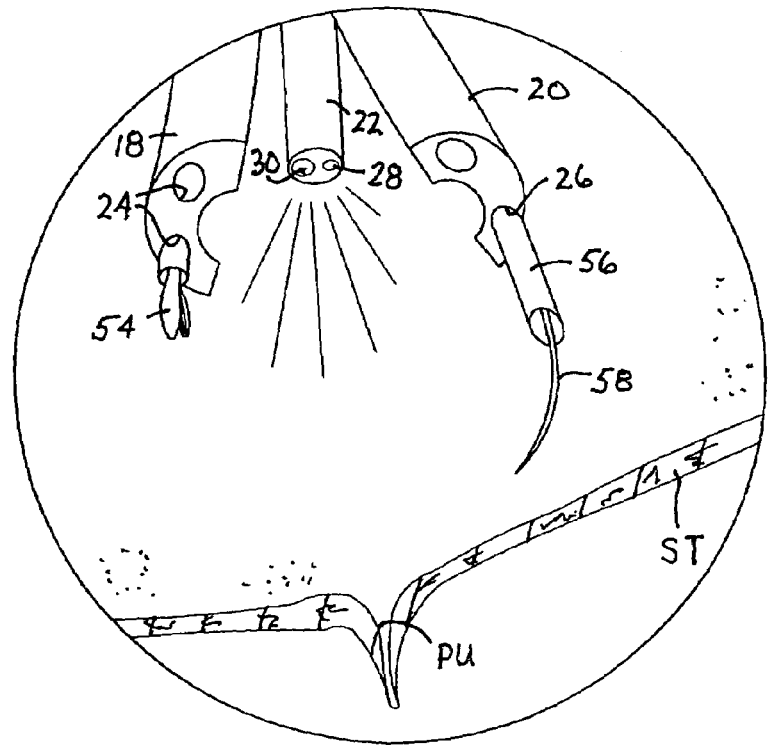

As depicted in FIG. 4C, a flexible endoscopic forceps 54 is inserted into the patient's stomach ST via a channel 24 of working segment 18, while a tubular member 56 carrying or guiding a suturing needle 58 is introduced into stomach ST via a channel 26 of working segment 20. Needle 58 may be made of a superelastic or shape memory Nitinol material so that the needle automatically assumes an arcuate configuration upon ejection from tubular member 56.

Figure 4D:
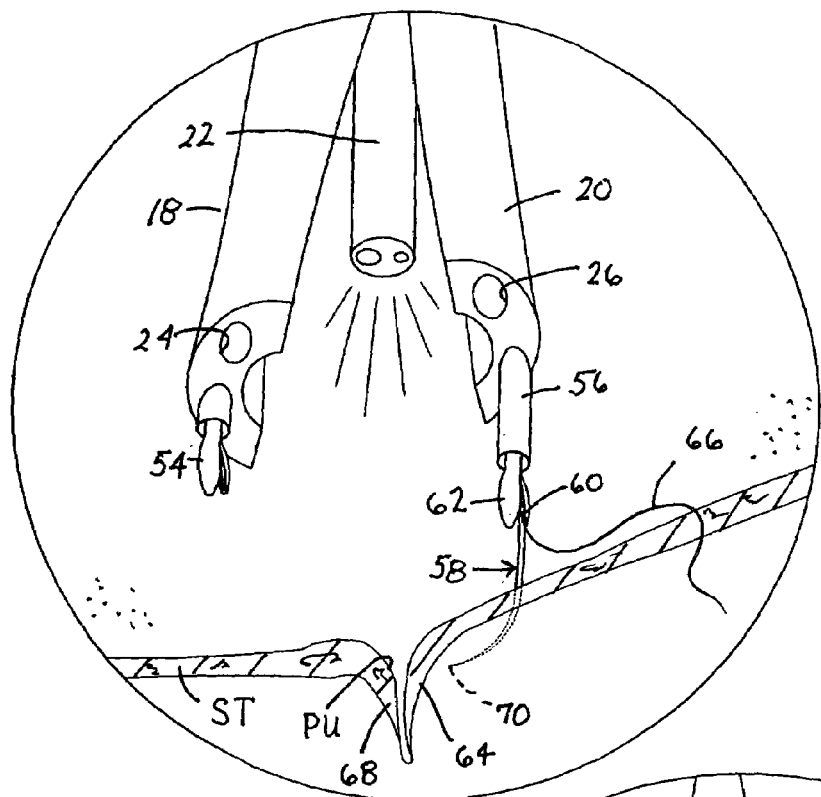

As depicted in FIG. 4D, needle 58 is held at its proximal or rear end 60 by a grasping forceps 62. Forceps 62 is pushed through tubular member 56 to insert needle 58 into stomach tissues 64 on one side of ulcer PU. A suture thread 66 is entrained to the needle 58 at the rear end 60 thereof.

Figure 4E:
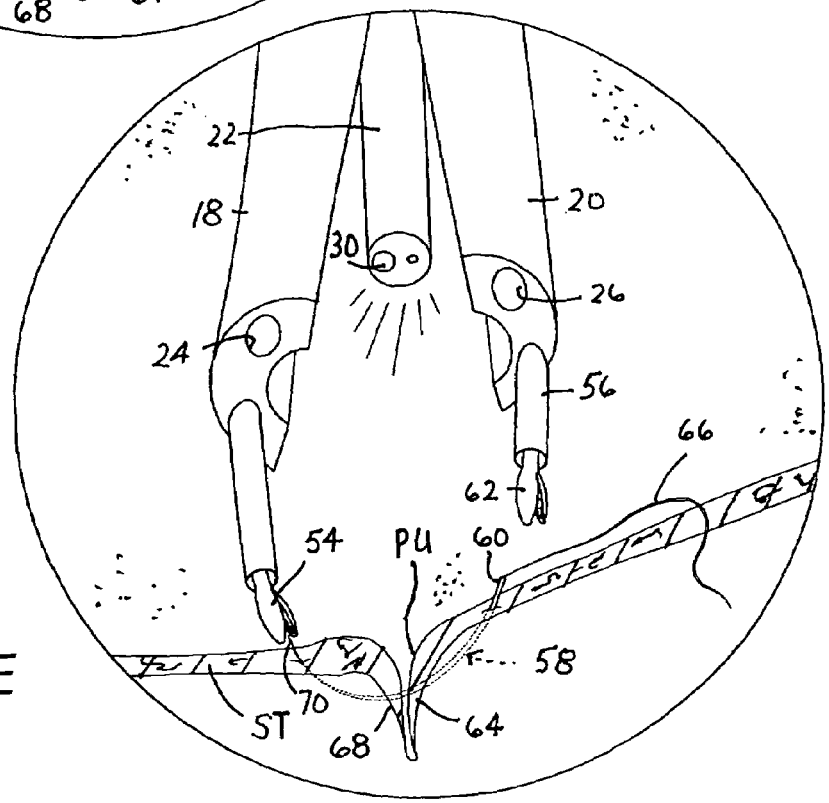
Figure 4F:
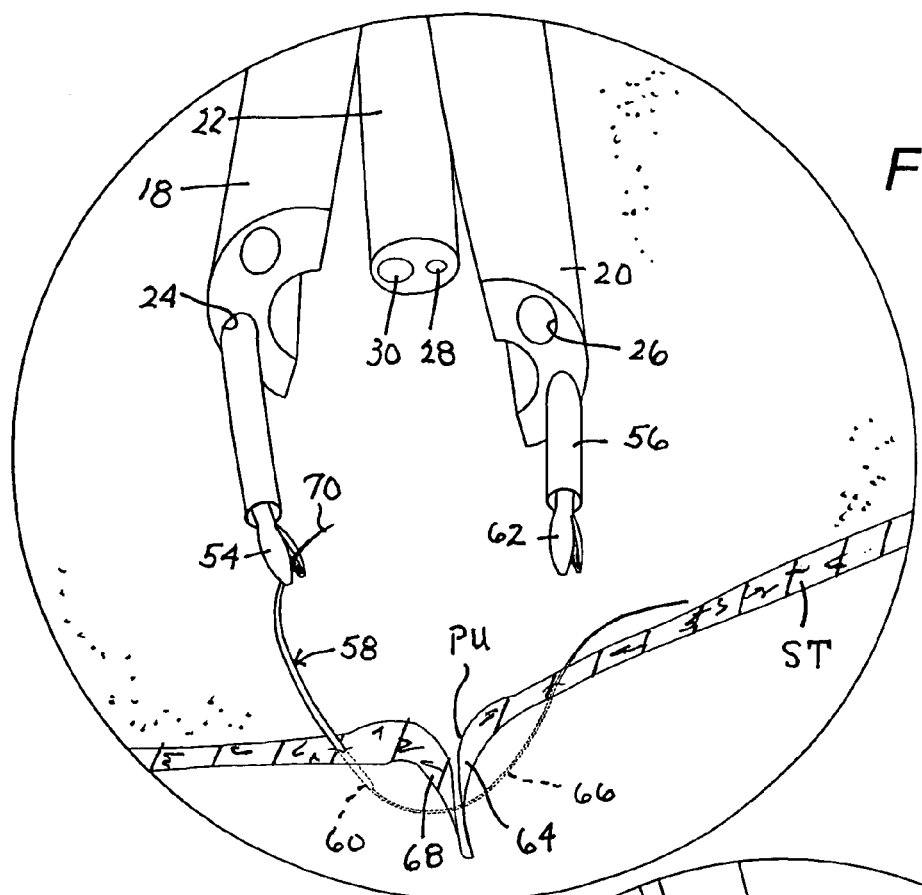
Figure 4G:
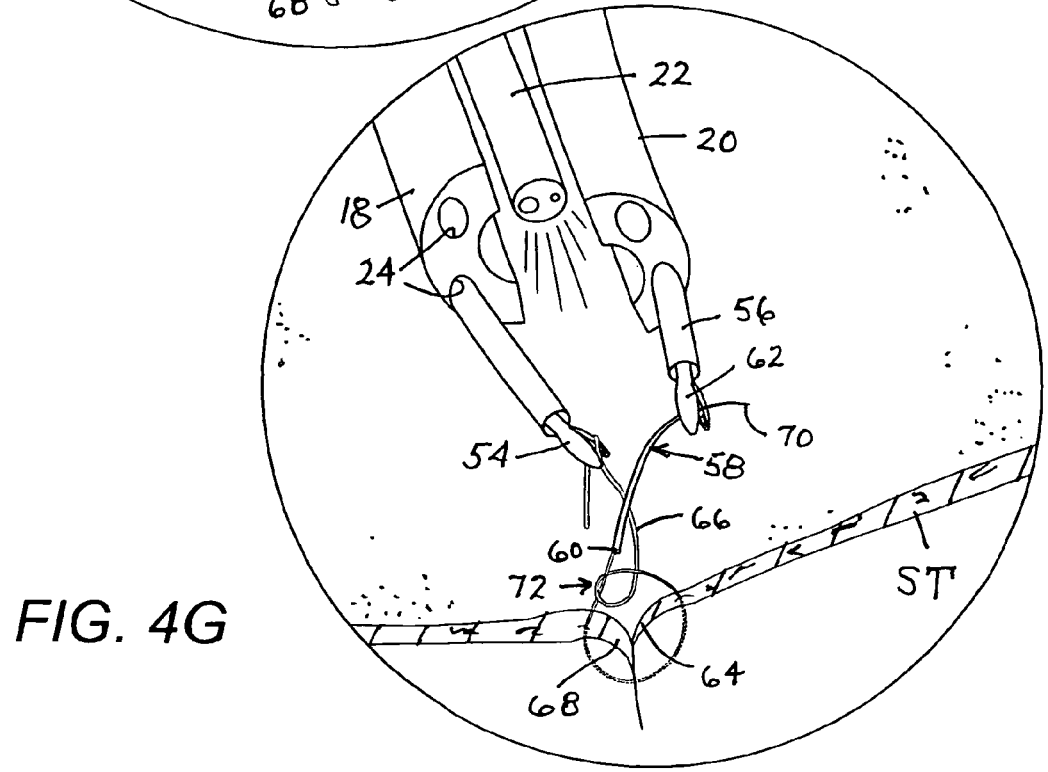

Needle 58 is pushed through tissues 64 and then through stomach tissues 68 on the other side of the perforated ulcer PU, as depicted in FIG. 4E. Upon an emergence of a sharp tip 70 of needle 58 from tissues 66, the respective surgeon or endoscopist manipulates forceps 54 to grasp tip 70. As illustrated in FIG. 4F, forceps 54 and working segment 18 are then further operated to withdraw needle 58 from tissues 68 and thereby pull suture thread 66 through tissue 64 and 68. The surgeons or endoscopists then cooperate, as shown in FIG. 4G, in maneuvering working segments 18 and 20 and forceps 54 and 62 to tie a knot 72 into suture thread 66.

Figure 4H:
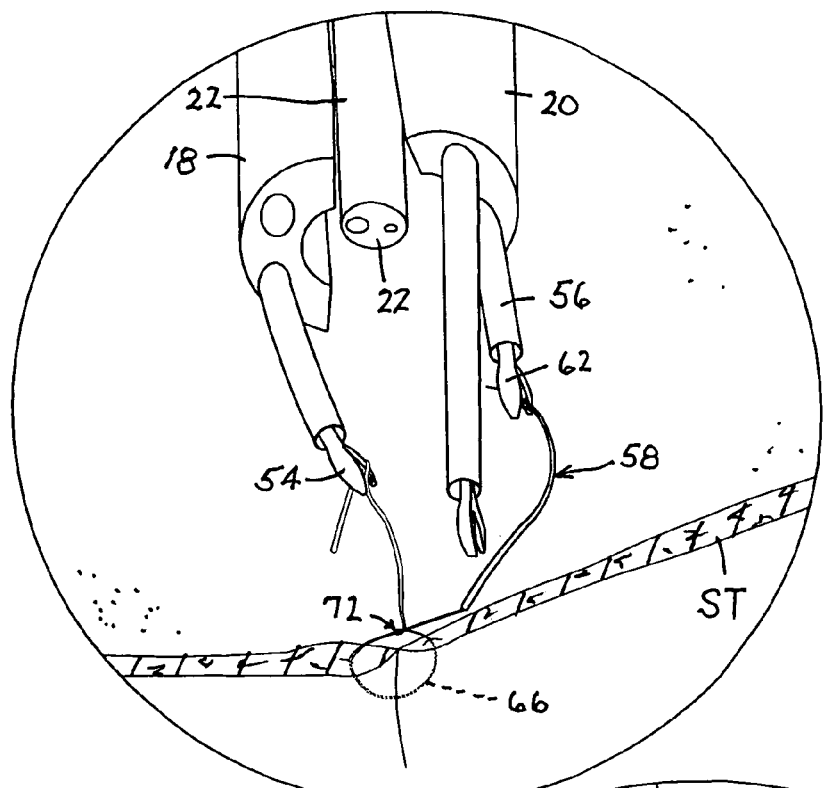
Figure 4I:
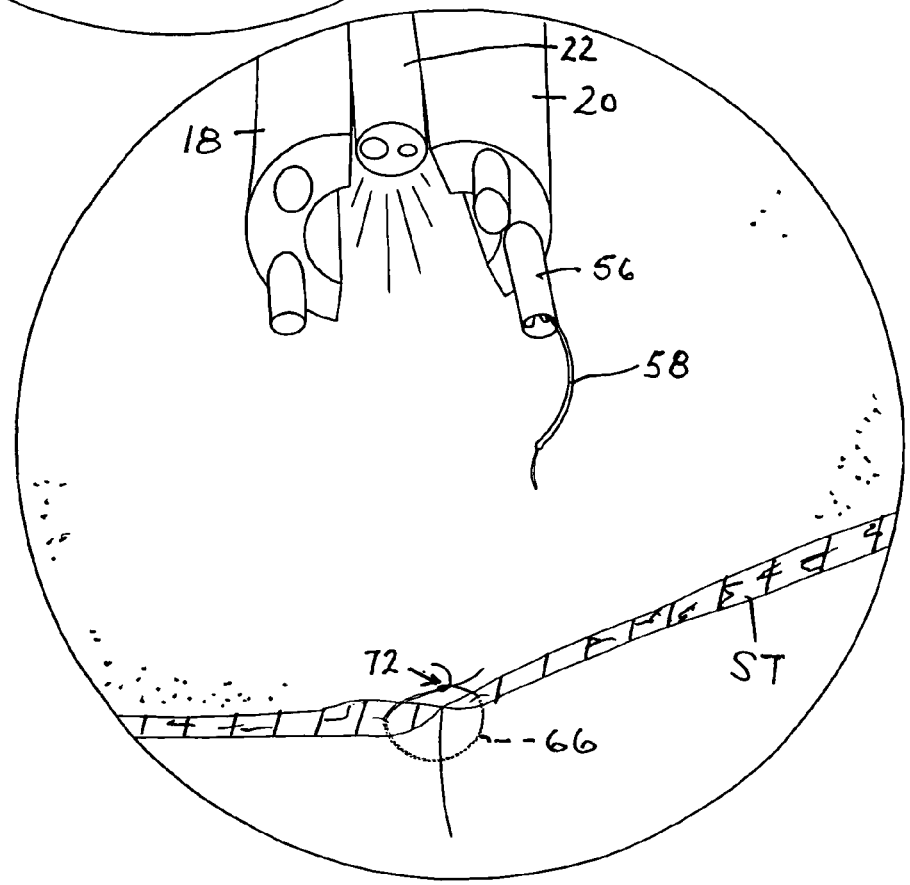
Figure 4J:
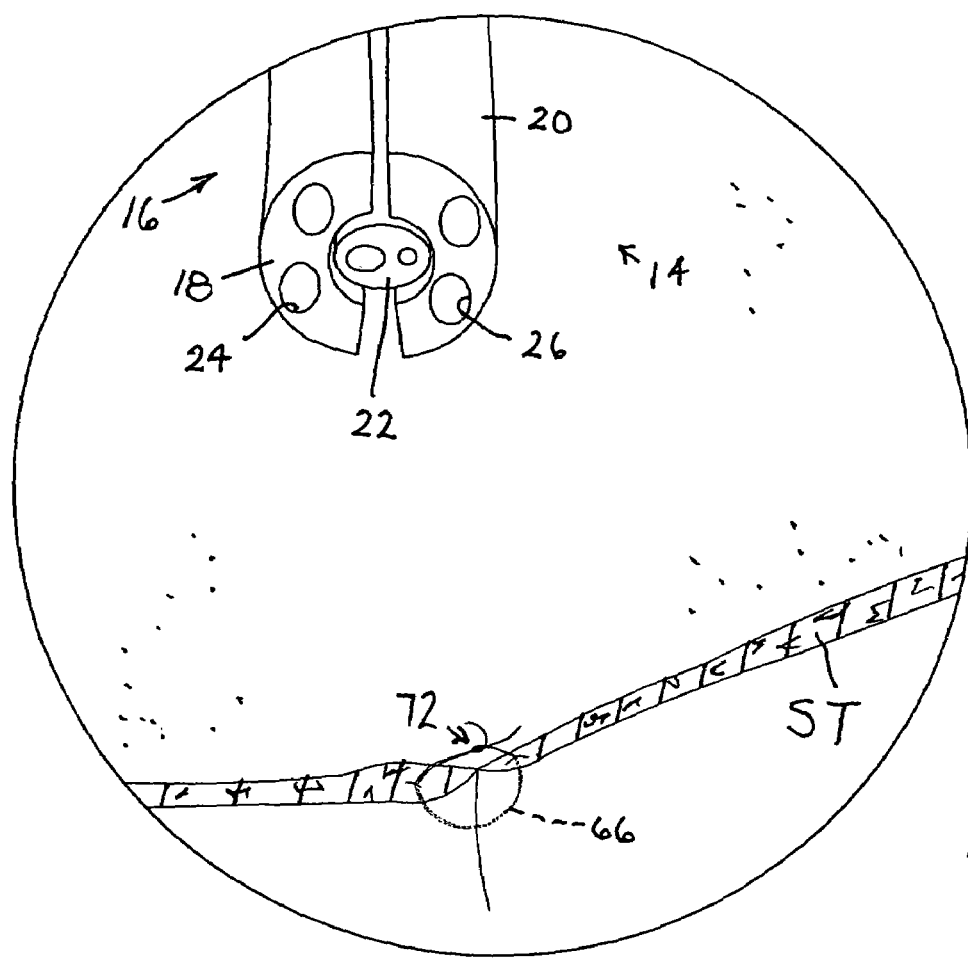

After the tying of knot 72 is completed, as shown in FIG. 4H, an endoscopic scissors 74 is introduced into the patient's stomach ST via a channel 26 (or 24) of working segment 20 (or 18). Scissors 72 is operated, from outside the patient, to sever suture 66. The various endsocopic instruments, 54, 56, 62, 74 are retracted into the respective channels 24 and 26 of working segments 18 and 20 (FIG. 4I) whereupon the endoscope insertion member 14 is ready for extraction from the patient (FIG. 4J) through the esophagus ES (FIG. 4A).

Figure 5A:
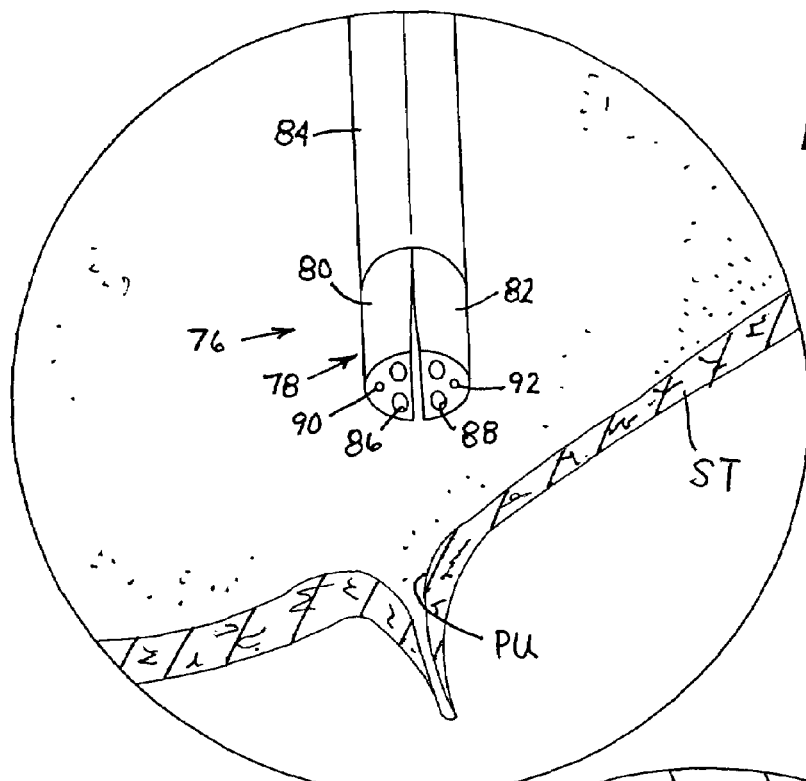
FIG. 5A is a schematic view similar to FIG. 4B, showing a distal end portion of another flexible fiberoptic endoscope in accordance with the present invention, where that other endoscope is performing the surgical procedure of FIGS. 4A–4J.
Figure 5B:
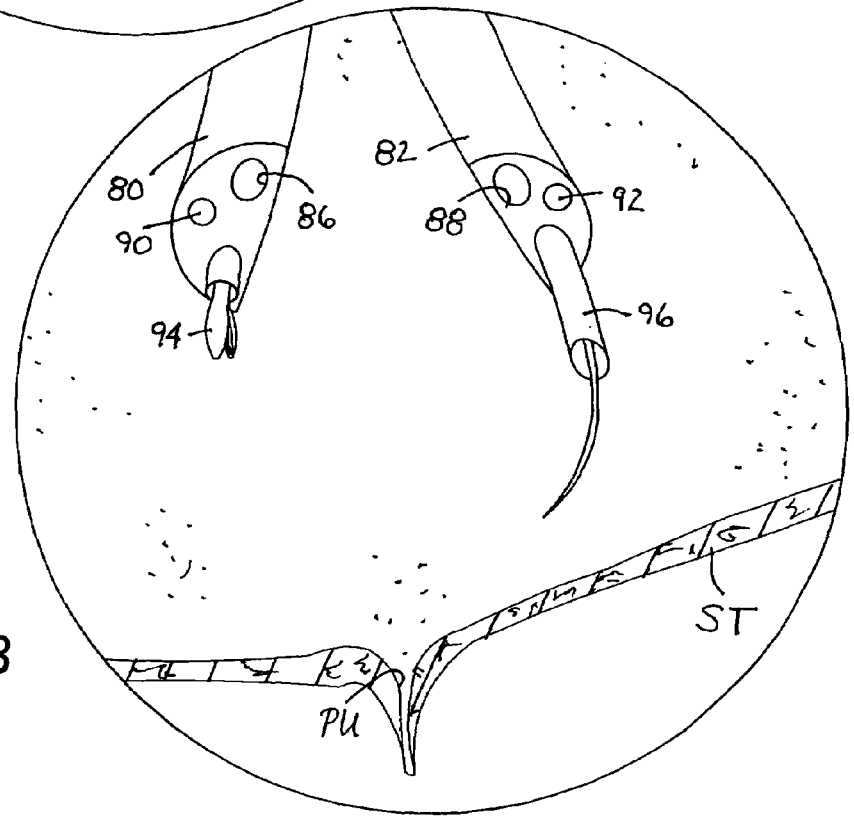
FIG. 5B is a schematic view showing the endoscope of FIG. 5A performing a step analogous to that depicted in FIG. 4C.

FIGS. 5A and 5B depict another endoscope insertion member 76 for performing endoscopic surgical operations. Endoscope insertion member 76 has a distal end portion 78 including two semi-cylindrical working segments 80 and 82 held together by a sheath 84 during an insertion or deployment procedure. Upon a removal of the sheath 84, the segments 80 and 82 are separated from one another (FIG. 5B) for independent maneuvering during a subsequently executed operation. Working segments 80 and 82 are provided with working channels 86 and 88 and visualization components 90 and 92. Endoscopic instruments 94 and 96 are inserted through channels 86 and 88 and then manipulated as described above with reference to FIG. 4A–4J.

Although the invention has been described in terms of particular embodiments and applications, one of ordinary skill in the art, in light of this teaching, can generate additional embodiments and modifications without departing from the spirit of or exceeding the scope of the claimed invention. For instance, a split endoscope in accordance with the present disclosure may have more than two working segments; illumination and visualization components may be disposed on different working or visualization segments; the coupling element binding the working segments may be an electrically operated latch or other locking member;

Accordingly, it is to be understood that the drawings and descriptions herein are proffered by way of example to facilitate comprehension of the invention and should not be construed to limit the scope thereof.

What is claimed is:

1. A flexible endoscope comprising an insertion member having a distal end portion split longitudinally into a plurality of independently operable working segments each provided with at least one longitudinally extending working channel, further comprising an additional segment containing illumination and image transmission components, said additional segment being the only segment provided with illumination and image transmission components.

2. The endoscope defined in claim 1, further comprising a coupling element operatively connected to said insertion member at least at said distal end portion to temporarily and releasably bind said working segments and said additional segment to one another.

3. The endoscope defined in claim 2 wherein said coupling element is a sheath.

4. The endoscope defined in claim 2 wherein said coupling element holds said working segments and said additional segment in a substantially tubular configuration.

5. The endoscope defined in claim 1 wherein said additional segment is cylindrical and centrally disposed with respect to said working segments, said working segments being annular sections in cross-section, said working segments surrounding said additional segment.

6. The endoscope defined in claim 1 wherein said working segments and said additional segment are operatively connected to respective control heads disposed at a proximal end of said insertion member, said working segments and said additional segment all being independently movable in response to operation of the respective control heads.

7. The endoscope defined in claim 1 wherein at least one segment taken from the group consisting of said working segments and said additional segment is longitudinally displaceable relative to other segments taken from said group.

8. The endoscope defined in claim 1 wherein at least one of said working segments includes a plurality of longitudinally extending working channels.

9. The endoscope defined in claim 1 wherein said working segments are permanently bound to one another at a location proximally removed from distal tips of said working segments.

10. A flexible endoscope comprising an insertion member having a distal end portion split longitudinally into a plurality of independently operable working segments each provided with at least one longitudinally extending working channel, further comprising a coupling element operatively connected to said insertion member at least at said distal end portion to temporarily and releasably bind said working segments to one another.

11. The endoscope defined in claim 10 wherein said coupling element is a sheath surrounding said working segments.

12. The endoscope defined in claim 10 wherein said coupling element holds said working segments in a substantially tubular configuration.

13. A flexible endoscope comprising an insertion member having a distal end portion split longitudinally into a plurality of independently operable working segments each provided with at least one longitudinally extending working channel, wherein said working segments are operatively connected to respective control heads disposed at a proximal end of said insertion member, said working segments being independently movable in response to operation of the respective control heads.

14. The endoscope defined in claim 13 wherein a proximal end portion of said insertion member divides into a plurality of separate longitudinally extending sections, said control heads being attached to respective ones of said sections.

15. A flexible endoscope comprising an insertion member having a distal end portion split longitudinally into a plurality of independently operable working segments each provided with at least one longitudinally extending working channel, wherein at least one of said working segments is longitudinally displaceable relative to another of said working segments.

16. A flexible endoscopic method comprising:
introducing an insertion member of a flexible endoscope into a patient, said insertion member having illumination and image transmission components;
thereafter, while maintaining a distal end portion of the endoscope in the patient, separating said distal end portion into a plurality of independent longitudinally extending working segments each having at least one longitudinally extending working channel;
passing a plurality of flexible endoscopic surgical instruments through the channels of the working segments;
while visualizing internal body tissues of the patient via the illumination and image transmission components, operating the surgical instruments via the respective working segments to perform a surgical operation on said internal body tissues; and
independently maneuvering the separated working segments inside the patient to enable the performance of the surgical operation,
wherein the maneuvering of the separated working segments includes actuating respective control heads located at a proximal end of the endoscope.

17. The method defined in claim 16 wherein the introducing of said insertion member into the patient includes inserting said working segments with a coupling element connected thereto to bind said working segments, further comprising releasing said coupling element from said working segments prior to the separating of said distal end portion into said working segments.

18. The method defined in claim 17 wherein said coupling element is a sheath at least partially surrounding said working segments during the introducing of said insertion member into the patient, the releasing of said coupling element including removing said sheath from said working segments.

19. The method defined in claim 18 wherein the removing of said sheath includes sliding said sheath in a proximal direction to uncover said working segments.

20. The method defined in claim 16, further comprising operating an additional control head at said proximal end of the endoscope to maneuver an additional segment of said distal end portion containing the illumination and image transmission components.

21. The method defined in claim 20, further comprising sliding one of said working segments in a longitudinal or axial direction relative to another of said working segments.

22. The method defined in claim 16, further comprising sliding one of said working segments in a longitudinal or axial direction relative to another of said working segments.

23. The method defined in claim 16 wherein said surgical operation is taken from the group consisting of suturing, cutting, tying, retracting.

\* \* \* \* \*